(12) United States Patent
Hajirasouliha

(10) Patent No.: US 8,465,285 B2
(45) Date of Patent: Jun. 18, 2013

(54) DENTAL FULCRUM

(76) Inventor: Zoya Hajirasouliha, Tarzana, CA (US)

( * ) Notice: Subject to any disclaimer, the term of this patent is extended or adjusted under 35 U.S.C. 154(b) by 0 days.

(21) Appl. No.: 13/333,839

(22) Filed: Dec. 21, 2011

(65) Prior Publication Data

US 2012/0164598 A1 Jun. 28, 2012

Related U.S. Application Data

(60) Provisional application No. 61/426,930, filed on Dec. 23, 2010.

(51) Int. Cl.
*A61B 5/117* (2006.01)

(52) U.S. Cl.
USPC ............. 433/229; 433/140; 433/163

(58) Field of Classification Search
USPC ............. 433/163, 49, 140, 141, 216, 215, 433/229, 25, 1, 148–149, 136–139; 132/308, 132/321, 329; 15/167.1, 244.1, 104.93, 244.4; 601/139, 136; 2/81, 21; 248/118, 118.1, 118.3, 248/118.5, 312.1; 128/112.1–120.1; 600/237–244
See application file for complete search history.

(56) References Cited

U.S. PATENT DOCUMENTS

| | | | |
|---|---|---|---|
| 1,721,334 A * | 7/1929 | Dillman | 604/77 |
| 3,705,585 A * | 12/1972 | Saffro | 604/385.01 |
| 4,585,416 A * | 4/1986 | DeNiro et al. | 433/140 |
| 5,860,182 A * | 1/1999 | Sareyani | 15/114 |
| 6,634,884 B2 * | 10/2003 | Phillips | 433/138 |
| 2006/0141105 A1 * | 6/2006 | Derrieu et al. | 426/132 |
| 2011/0091839 A1 * | 4/2011 | Niesten et al. | 433/216 |

FOREIGN PATENT DOCUMENTS

EP 2135527 A1 * 12/2009

OTHER PUBLICATIONS

Machine Translation of EP 2135527 A1.*

* cited by examiner

*Primary Examiner* — Cris L Rodriguez
*Assistant Examiner* — Edward Moran

(57) ABSTRACT

A dental fulcrum composed of soft material, such as foam, containing a slit for the insertion of incisors, and used as a pivot for scaling, or other treating, teeth by an oral hygienist or dentist. The dental fulcrum protects the fingers of an oral hygienist or dentist from calluses, or loss of sensitivity over time, while at the same time providing friction to reduce the risk of injury caused by fingers slipping on wet incisors. The device may be disposable or reusable, depending on the material used. Foam provides the additional benefit of absorbing saliva to further reduce the risk of slippage.

16 Claims, 4 Drawing Sheets

DENTAL FULCRUM

CROSS-REFERENCE TO RELATED APPLICATION

Applicant claims the benefit of provisional patent application No. 61/426,930 filed on Dec. 23, 2010.

FEDERALLY SPONSORED RESEARCH

Not Applicable

SEQUENCE LISTING OR PROGRAM

Not Applicable

STATEMENT REGARDING COPYRIGHTED MATERIAL

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND

The invention relates to the field of dentistry and oral hygiene, in particular, a support device that assists with dental treatment involving the mandibular (lower) teeth by providing a finger rest to act as a fulcrum on the sharp edges of the incisors (front teeth), or to act as a fulcrum in the case of loose incisors or no incisors.

Oral hygienists and dentists must often treat the lower mandibular teeth, for example, to scale off calculus, or clean off tartar. To do this, the oral hygienist or dentist must rest his or her fingers on the incisors in order to pivot a dental instrument. Over time, calluses form on the fingers of the hygienist or dentist due to the sharpness of the incisors. This also causes a loss of sensation.

Resting fingers on the incisors to pivot a dental instrument is also dangerous for the patient due to risk of slippage and loss of control of the dental instrument resulting from a combination of force, saliva, and use of a latex glove.

On the other extreme, some patients have no incisors, and thus no place to pivot a dental instrument, or loose teeth (periodontal disease) on which pressure cannot be applied without causing'pain to the patient. The present invention can therefore additionally serve as a fulcrum on which to pivot a dental instrument where the patient has no incisors or loose incisors.

A need therefore arises to provide protection to the fingers of an oral hygienist or dentist, improve the safety of patients by reducing the risk of slippage and loss of control of a dental instrument while treating the lower mandibular teeth, and provide a means to pivot a dental instrument where the patient has no incisors or loose incisors.

The need is satisfied in the form of the present invention which consists of a dental fulcrum, preferably of soft foam material capable of absorbing saliva, with a notch or slit in the center for insertion, wherein the dental fulcrum is placed over the incisors through the slit. The dental fulcrum reduces the risk of slippage because the soft foam provides friction against slippage, while also absorbing saliva, and avoids injury to the hands of the oral hygienist or dentist whose fingers may now rest on the soft foam to pivot a dental instrument.

While the dental fulcrum is designed for the lower front teeth, it is to be understood that it may be used for the upper teeth, as well as other teeth as a dentist or oral hygienists deems fit.

DRAWINGS

SUMMARY

Figure 1:
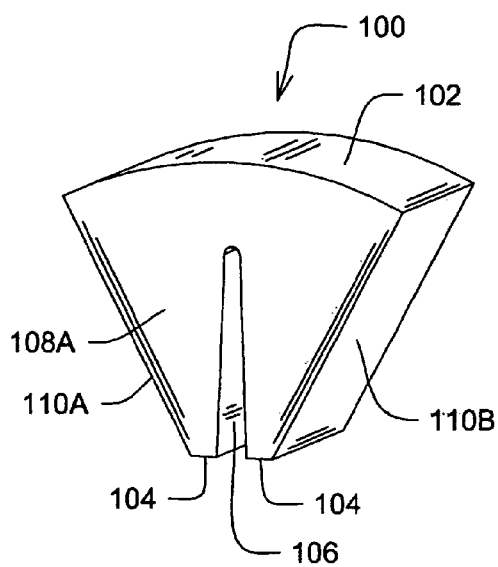
FIG. 1 is a perspective view of the preferred embodiment of a dental fulcrum of the present invention.

The present invention seeks to provide a more comfortable and safer means of treating the lower mandibular teeth in the form of a device made of a soft material with a notch or slit in the middle for insertion over the incisors. This device is a dental fulcrum onto which an oral hygienist or dentists may rest his or her fingers to pivot a dental instrument. While the device may consist of any soft material for providing support, including hard plastic, aluminum, wax, gum, or rubber, the preferred material is foam, which provides sufficient friction against slippage while also absorbing saliva to reduce slippage. This improves safety for the patient. The use of soft material also protects the fingers of an oral hygienist or dentist from calluses. The larger the width of the device, the lower the risk of slippage as the device provides a greater area of pivot for the fingers and can absorb more saliva.

The device may be disposable or reusable. If disposable, the device would more likely be in the form of a soft foam. If reusable, hard plastic, aluminum or high density rubber may be used so that the device can withstand a cold sterilizer or the high temperatures and pressures of an autoclave.

DESCRIPTION

FIGS. 1-6 illustrates the preferred embodiment of a dental fulcrum 100 made of soft material, preferably foam, having a curved top 102, facing the occlusal direction, and a flat bottom 104, facing the gingival direction, in which the curved top 102 has a longer length than the flat bottom 104. In addition, the fulcrum 100 has a front side 110B, facing the lips of a patient, a back side 110A, facing the tongue of a patient, a left side 108A and a right side 108B. A notch or slit 106 is disposed in the center of the dental fulcrum 100, intersects the surface of the flat bottom 104, and cuts across the dental fulcrum so that openings exist on the left side 108A and right side 108B. The slit 106 and openings on the left side 108A and the right side 108B allow the dental fulcrum 100 to be placed on incisors and to be moved along the length of incisors 112. The notch or slit 106 is long enough and wide enough for the insertion of incisors 112. The front side 110B and back side 110A, are slanted inward in the direction of the flat bottom 104. When pressure is placed on the surface of the curved top 102, the slanted front side 110B and slanted back side 110A will tend to close inward so that the slit 106 will grasp the incisors 112 (and gums) harder and stabilize the dental fulcrum on the incisors 112.

Figure 6:
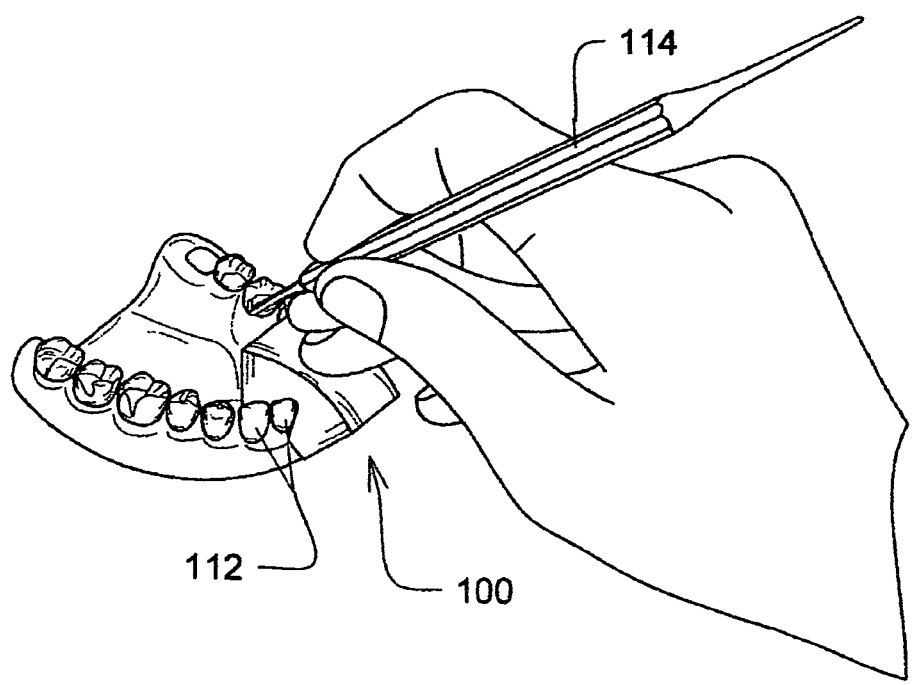
FIG. 6 is an illustration of the dental fulcrum in use by an oral hygienist while scaling teeth.
Figure 7:
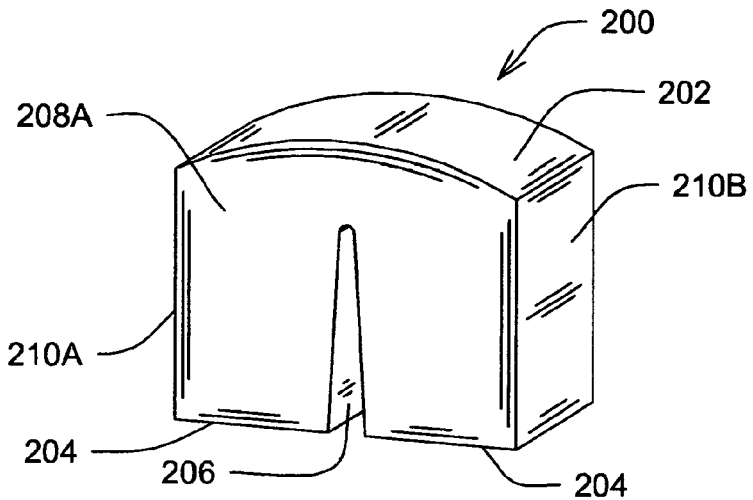
FIG. 7 is a perspective view of an alternate embodiment of a dental fulcrum of the present invention.
Figure 8:
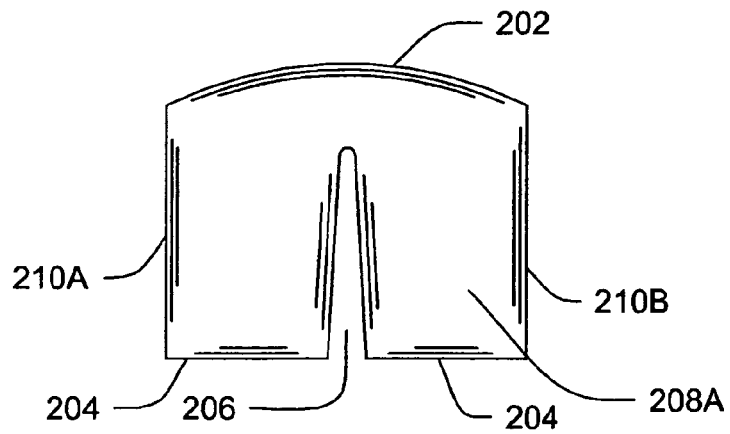
FIG. 8 is a side view of the alternate embodiment of the dental fulcrum.
Figure 9:
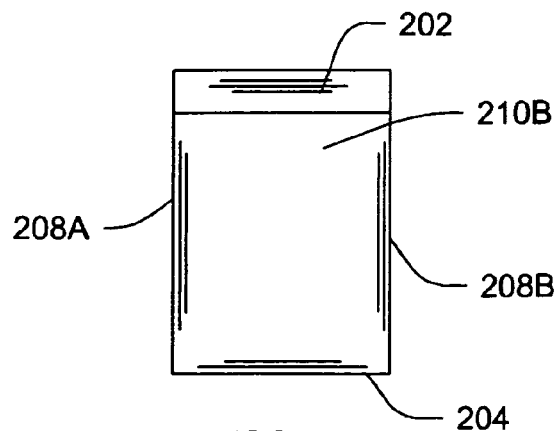
FIG. 9 is a front view of the dental fulcrum, which is the same as the back view.
Figure 10:
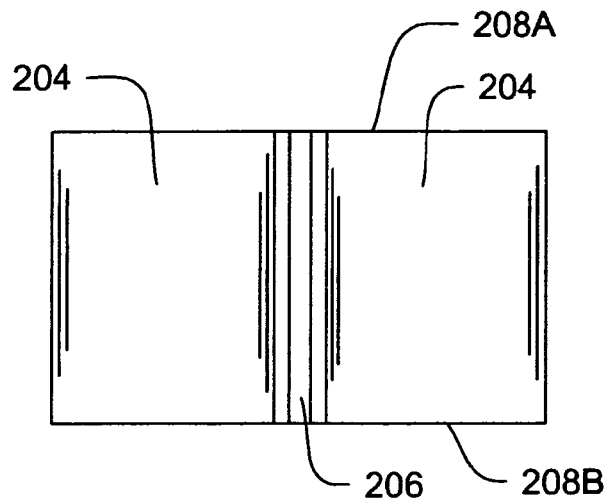
FIG. 10 is a bottom view of the dental fulcrum of the alternate embodiment.
Figure 11:
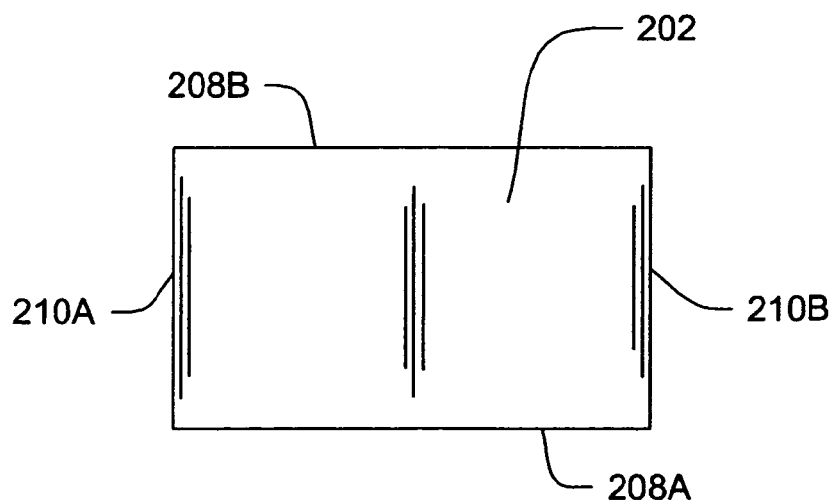
FIG. 11 is a top view of the dental fulcrum of the alternate embodiment.

FIG. 6 illustrates the dental fulcrum 100 in use. The dental fulcrum 100 is placed on the incisors 112 through the notch or slit 106. An oral hygienist or dentist may rest his or her fingers on the dental fulcrum 100 as a pivot when scaling or treating teeth with a dental instrument 114. This avoids calluses on the fingers and reduces the risk of the fingers slipping on the incisors, as the dental fulcrum provides friction against slippage, and when foam material is used, absorbs saliva.

FIGS. 7-11 illustrates an alternate embodiment of the dental fulcrum 200. The fulcrum 200 has a front side 210B, facing the lips of a patient, a back side 210A, facing the tongue of a patient, a curved top 202, facing the occlusal direction, a flat bottom 204, facing the gingival direction, a left side 208A and a right side 208B. The front side 210B and the back side 210A, are not slanted inward toward the flat bottom 204 and the curved top 202 and flat bottom 204 are of substantially the same length. The fulcrum 200 has a slit 206 configured and orientated the same as with the fulcrum 100. The surface area of the alternate embodiment is greater than the preferred embodiment and therefore, may be more bulky. When pressure is placed on the surface of the curved top 202 it is not transferred toward the slit 206 but instead is transferred toward the flat bottom 204 (and subsequently on the lips or tongue). The choice of the preferred embodiment over the alternate embodiment may depend on numerous factors, including gum sensitivity, size of mouth or teeth, patient's comfort, size of fingers, etc.

Figure 2:
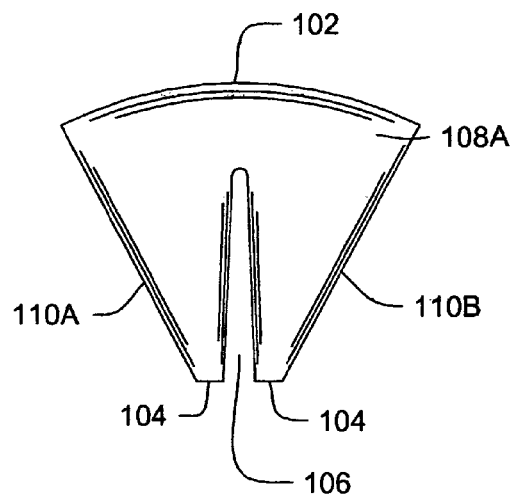
FIG. 2 is a side view of the dental fulcrum.
Figure 3:
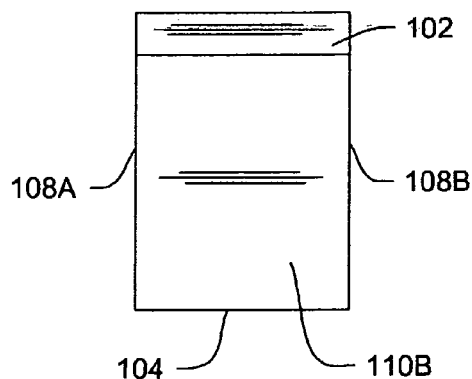
FIG. 3 is a front view of the dental fulcrum which is the same as the back view.
Figure 4:
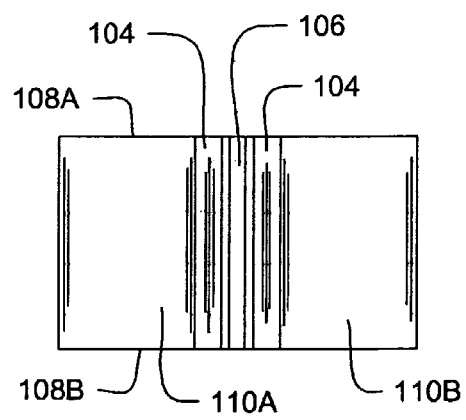
FIG. 4 is a bottom view of the dental fulcrum.
Figure 5:
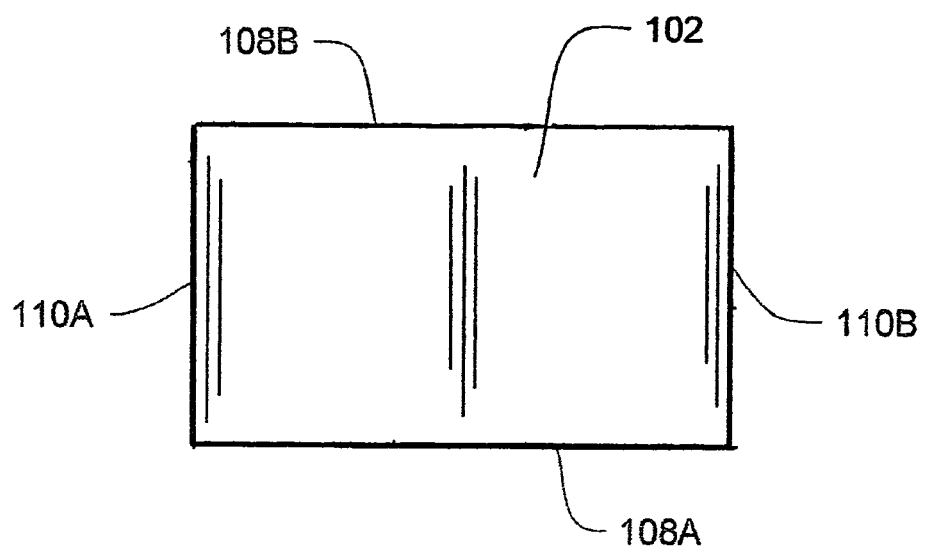
FIG. 5 is a top view of the dental fulcrum.

The preferred dimensions for the preferred embodiment, as viewed from FIG. 2, are as follows: The slit 106 is 2 mm in width at the top end and 3 mm wide at the bottom end (flat bottom 104), and 6 mm high. The height of the dental fulcrum 100 (front side 110B and back side 110A) is 12 mm. The width of the curved top 102 is 20 mm from one end to the other end. The width of the flat bottom 104 is 11 mm, which includes the 3 mm wide opening formed by the slit 106. The length of the dental fulcrum 100, (side 108A to side 108B) should be sufficient to cover the incisors. Note that located on the front side of the mouth there are four incisors on the top and four incisors on the bottom for a total of 8 incisors.

All features disclosed in this specification, including any accompanying claims, abstract, and drawings, may be replaced by alternative features serving the same, equivalent or similar purpose, unless expressly stated otherwise. Thus, unless expressly stated otherwise, each feature disclosed is one example only of a generic series of equivalent or similar features.

Although preferred embodiments of the present invention have been shown and described, various modifications and substitutions may be made thereto without departing from the spirit and scope of the invention. Accordingly, it is to be understood that the present invention has been described by way of illustration and not limitation.

What is claimed:

1. A dental fulcrum for supporting the weight of one or more fingers of a dental professional and a dental instrument used by the dental professional during a dental procedure on a patient, the dental fulcrum comprising:

a front side constructed and arranged to face the lips of the patient and a back side constructed and arranged to face the tongue of the patient, said front side and said back side being of the same length and width;

a left side and a right side having the same length and width;

a top side constructed and arranged to face the occlusal direction and a bottom side constructed and arranged to face the gingival direction;

a slit disposed through and creating openings onto said left side and said right side of said dental fulcrum, said slit constructed and arranged to intersect and to open onto said bottom side;

said slit being formed for and enabling the insertion of at least one incisor therein;

said slit configured to maintain sufficient surface contact with at least one incisor to provide resistance to fore and aft motion of the dental fulcrum during use;

wherein said slit and said openings in the left and right sides have smooth, flat and linearly tapered surfaces expanding outwardly in the gingival direction towards said bottom side;

wherein said front and back sides have smooth, flat, rectangular surfaces slanted inwardly towards each other;

wherein said left and right sides have smooth and flat trapezoidal surfaces and wherein said left and right sides are perpendicular to said top side;

wherein said top side has a smooth arcuate surface that is larger than said bottom side whereby, when said slit portion of said dental fulcrum is placed on at least one incisor of the patient, a stable surface is provided for supporting the weight of one or more fingers of the dental professional and the dental instrument used by the dental professional.

2. The fulcrum as defined in claim 1, wherein the fulcrum is composed of a resilient material.

3. The fulcrum as defined in claim 1, wherein said slit has fore and aft side surfaces and wherein said side surfaces of said slit are planar and divergent with respect to each other.

4. The fulcrum as defined in claim 1, wherein the configuration of said slit is such that when force is applied to said top side, said slit applies a corresponding greater force to the associated incisors.

5. The fulcrum as defined in claim 1, wherein the fulcrum is composed of a material selected from a group including foam, plastic, aluminum, wax, gum, rubber and any other material with sufficient density to withstand cold sterilizers and high temperatures and pressures of an autoclave.

6. A dental fulcrum sufficient to support the weight of one or more fingers of a dental professional and a dental instrument, the fulcrum comprising:

a front side adapted to face the lips of a patient and a back side adapted to face the tongue of a patient;

said front side and said back side being of the same length and width;

a left side and right side having the same length and width;

a top side adapted to face the occlusal direction and a bottom side adapted to face the gingival direction;

a slit, disposed through said left and said right sides of the fulcrum, intersecting and opening to said bottom side and creating openings on said left and said right sides, said slit being long enough and wide enough for the insertion of at least one incisor;

wherein the fulcrum is composed of a soft material;
wherein said slit and said openings in the left and right sides have smooth, flat and linearly tapered surfaces, expanding outwardly in the gingival direction towards said bottom side;
wherein said front and back sides have smooth, flat, rectangular surfaces slanted inwardly towards each other;
wherein said left and right sides have smooth and flat trapezoidal surfaces and wherein said left and right sides are perpendicular to said top side;
wherein said top side has a smooth arcuate surface that is larger than said bottom side.

7. The dental fulcrum as defined in claim 6, wherein said soft material is foam.

8. The dental fulcrum as defined in claim 6, wherein said soft material is selected from a group including wax, gum, rubber, foam or other material with sufficient density to withstand cold sterilizers and high temperatures and pressures of an autoclave.

9. The dental fulcrum as defined in claim 6, wherein the fulcrum is adapted to be placed over at least one incisor of a patient and configured to resist fore and aft motion of the fulcrum, thereby providing a stable platform for one or more of a dental professional's fingers and dental instrument, and thus protecting the dental professional and the patient from possible accidental injury.

10. A method for supporting the weight of one or more fingers of a dental professional and a dental instrument used by the dental professional during a dental procedure on a patient, said dental fulcrum comprising the steps of:
    providing a dental fulcrum for supporting the weight of one or more fingers of a dental professional and a dental instrument used by the dental professional during a dental procedure on a patient, said fulcrum comprising:
        a front side constructed and arranged to face the lips of the patient and a back side constructed and arranged to face the tongue of the patient, said front side and said back side being of the same length and width;
        a left side and a right side having the same length and width;
        a top side constructed and arranged to face the occlusal direction and a bottom side constructed and arranged to face the gingival direction;
        a slit disposed through and opening onto said left side and said right side of said dental fulcrum, said slit constructed and arranged to intersect and to open onto said bottom side;
        said slit being formed for and enabling the insertion of at least one incisor therein;
        said slit configured to maintain sufficient contact surface with at least one incisor to provide resistance to fore and aft motion of the dental fulcrum during use;
    placing said fulcrum on at least one incisor of a dental patient by inserting the at least one incisor into the slit;
    resting at least one finger of the dental professional on said fulcrum;
    performing a dental procedure; and
    removing said dental fulcrum from said at least one incisor;
    whereby, a more precise dental procedure can be performed and the risk of an accident can be reduced.

11. The method as defined in claim 10 wherein said fulcrum is composed of a resilient material.

12. The method as defined in claim 10 wherein said top side is arcuate.

13. The method as defined in claim 10 wherein said slit has fore and aft side surfaces and wherein said side surfaces of said slit are planar and divergent with respect to each other.

14. The method as defined in claim 10 wherein said front and back sides are planar and divergent with respect to each other.

15. The method as defined in claim 10, wherein the configuration of said slit is such that when a force is applied to said top side, said slit applies a corresponding greater force to the associated incisors.

16. The method as defined in claim 10 wherein said fulcrum is composed of a material selected from a group including foam, plastic, aluminum, wax, gum, rubber and any other material with sufficient density to withstand cold sterilizers and high temperatures and pressures of an autoclave.

\* \* \* \* \*